US012758209B2

(12) United States Patent
Clark et al.

(10) Patent No.: US 12,758,209 B2
(45) Date of Patent: *Oct. 13, 2026

(54) KNOTLESS ANCHOR

(71) Applicant: TIGON MEDICAL, Millersville, MD (US)

(72) Inventors: Jeremy Clark, Millersville, MD (US); Umasuthan Srikumaran, Ellicott City, MD (US); Matthew Thompson, Washington, DC (US)

(73) Assignee: Tigon Medical, Millersville, MD (US)

( * ) Notice: Subject to any disclaimer, the term of this patent is extended or adjusted under 35 U.S.C. 154(b) by 75 days.

This patent is subject to a terminal disclaimer.

(21) Appl. No.: 18/629,382

(22) Filed: Apr. 8, 2024

(65) Prior Publication Data

US 2024/0252162 A1 Aug. 1, 2024

Related U.S. Application Data

(63) Continuation of application No. 17/015,992, filed on Sep. 9, 2020, now Pat. No. 11,950,774, which is a continuation of application No. 16/021,423, filed on Jun. 28, 2018, now Pat. No. 10,786,236.

(60) Provisional application No. 62/541,286, filed on Aug. 4, 2017.

(51) Int. Cl.

| | |
|---|---|
| ***A61B 17/04*** | (2006.01) |
| ***A61B 17/00*** | (2006.01) |
| ***A61B 17/06*** | (2006.01) |
| ***A61F 2/00*** | (2006.01) |
| ***A61F 2/08*** | (2006.01) |

(52) U.S. Cl.

CPC ........ *A61B 17/0401* (2013.01); *A61F 2/0811* (2013.01); *A61B 2017/00473* (2013.01); *A61B 2017/0403* (2013.01); *A61B 2017/0409* (2013.01); *A61B 2017/0412* (2013.01); *A61B 2017/0446* (2013.01); *A61B 2017/0453* (2013.01); *A61B 17/06166* (2013.01); *A61F 2002/0081* (2013.01); *A61F 2002/0858* (2013.01); *A61F 2002/0888* (2013.01); *A61F 2220/0016* (2013.01); *A61F 2230/0067* (2013.01)

(58) Field of Classification Search

None

See application file for complete search history.

(56) References Cited

U.S. PATENT DOCUMENTS 5,573,548 A * 11/1996 Nazre ................ A61B 17/0401 606/232
5,690,676 A * 11/1997 DiPoto .............. A61B 17/0401 606/232
5,733,307 A * 3/1998 Dinsdale ............ A61B 17/0401 606/232
6,508,830 B2 * 1/2003 Steiner ............... A61B 17/0401 606/232

(Continued)

*Primary Examiner* — Shaun L David

(74) *Attorney, Agent, or Firm* — BRAINSPARK ASSOCIATES, LLC

(57) ABSTRACT

Disclosed are devices, methods and/or systems for securing tissue to bone, including a suture anchor implant having a body through which a suture eyelet extends transversely, and one or more suture pinch slits extending proximally from the suture eyelet, the suture pinch slit(s) angled relative to the longitudinal axis of the anchor.

9 Claims, 15 Drawing Sheets

(56) References Cited

U.S. PATENT DOCUMENTS

| | | | | | |
|---|---|---|---|---|---|
| 6,517,542 | B1 * | 2/2003 | Papay | A61C 8/0022 | 606/232 |
| 6,520,980 | B1 * | 2/2003 | Foerster | A61B 17/0401 | 606/232 |
| 6,527,794 | B1 * | 3/2003 | McDevitt | A61F 2/0811 | 606/1 |
| 6,641,596 | B1 * | 11/2003 | Lizardi | A61F 2/0811 | 606/232 |
| 7,780,701 | B1 * | 8/2010 | Meridew | A61B 17/0401 | 606/232 |
| 7,879,072 | B2 * | 2/2011 | Bonutti | A61B 17/0487 | 606/232 |
| 9,101,355 | B2 * | 8/2015 | Lantz | A61B 90/03 | |
| 9,179,905 | B2 * | 11/2015 | Pamichev | A61B 17/0401 | |
| 10,426,456 | B2 * | 10/2019 | Pamichev | A61B 17/0401 | |
| 2003/0088250 | A1 * | 5/2003 | Colleran | A61B 17/0401 | 606/232 |
| 2003/0097150 | A1 * | 5/2003 | Fallin | A61B 17/0401 | 606/232 |
| 2003/0120309 | A1 * | 6/2003 | Colleran | A61B 17/0401 | 606/232 |
| 2004/0133239 | A1 * | 7/2004 | Singhatat | A61B 17/0401 | 606/232 |
| 2004/0138706 | A1 * | 7/2004 | Abrams | A61B 17/0401 | 606/232 |
| 2006/0178702 | A1 * | 8/2006 | Pierce | A61B 17/1617 | 606/232 |
| 2006/0235413 | A1 * | 10/2006 | Denham | A61B 17/0401 | 606/907 |
| 2006/0282081 | A1 * | 12/2006 | Fanton | A61B 17/0401 | 606/232 |
| 2007/0021781 | A1 * | 1/2007 | Jervis | A61B 17/06061 | 606/232 |
| 2007/0203498 | A1 * | 8/2007 | Gerber | A61B 17/0401 | 606/328 |
| 2007/0225719 | A1 * | 9/2007 | Stone | A61B 17/0642 | 606/232 |
| 2008/0255613 | A1 * | 10/2008 | Kaiser | A61F 2/0811 | 606/232 |
| 2008/0306511 | A1 * | 12/2008 | Cooper | A61B 17/0401 | 606/232 |
| 2009/0312794 | A1 * | 12/2009 | Nason | A61B 17/0401 | 606/232 |
| 2010/0004683 | A1 * | 1/2010 | Hoof | A61B 17/0401 | 606/232 |
| 2010/0016869 | A1 * | 1/2010 | Paulk | A61B 17/0469 | 606/232 |
| 2011/0071545 | A1 * | 3/2011 | Pamichev | A61F 2/34 | 606/139 |
| 2011/0112576 | A1 * | 5/2011 | Nguyen | A61B 17/0401 | 606/232 |
| 2011/0190815 | A1 * | 8/2011 | Saliman | A61B 17/0487 | 606/232 |
| 2012/0053626 | A1 * | 3/2012 | Koepke | A61B 17/0401 | 606/232 |
| 2012/0078300 | A1 * | 3/2012 | Mayer | A61B 17/0401 | 606/232 |
| 2013/0006276 | A1 * | 1/2013 | Lantz | A61B 17/0467 | 606/144 |
| 2013/0096611 | A1 * | 4/2013 | Sullivan | A61B 17/0485 | 606/232 |
| 2013/0103081 | A1 * | 4/2013 | Wolf | A61B 17/0401 | 606/232 |
| 2013/0103083 | A1 * | 4/2013 | Baird | A61B 17/0401 | 606/232 |
| 2013/0267998 | A1 * | 10/2013 | Vijay | A61B 17/0401 | 606/232 |
| 2014/0081323 | A1 * | 3/2014 | Hawkins | A61B 17/0401 | 606/232 |
| 2015/0201923 | A1 * | 7/2015 | Fan | A61B 17/0401 | 606/232 |

* cited by examiner

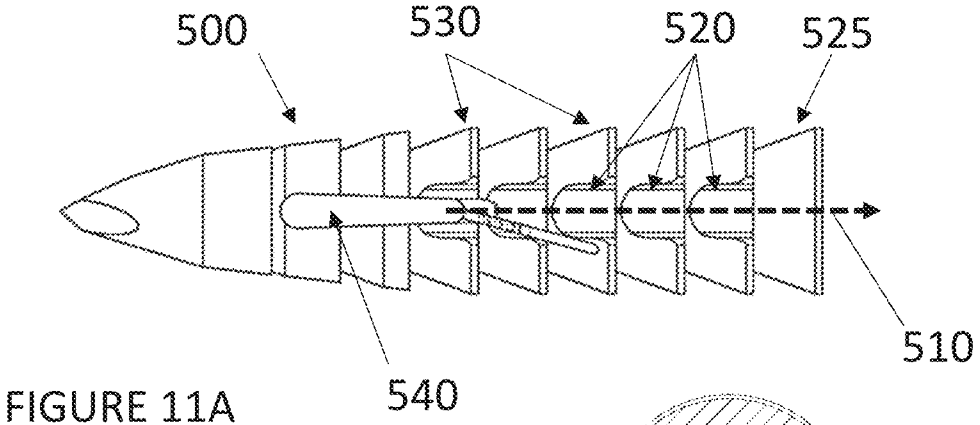
FIGURE 11A
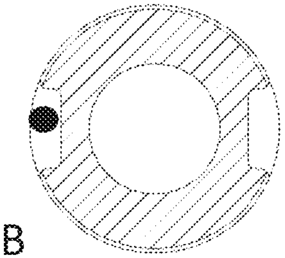
FIGURE 11B
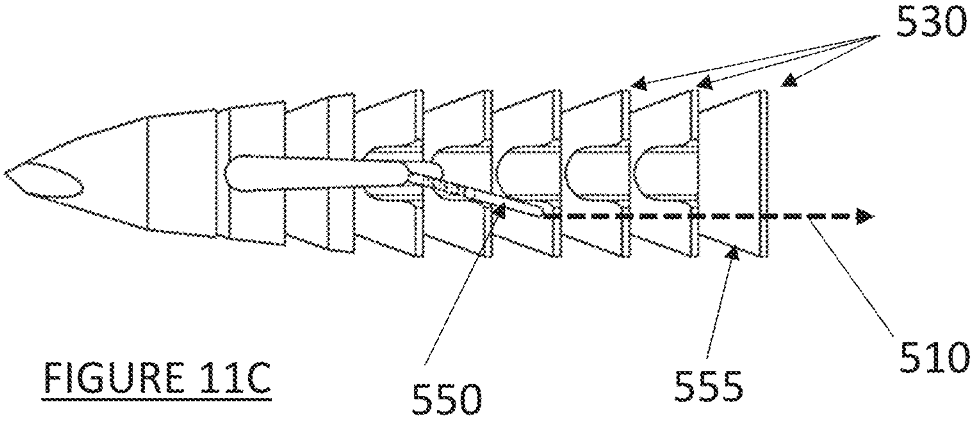
FIGURE 11C
FIGURE 11D
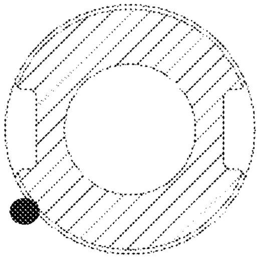

KNOTLESS ANCHOR

CROSS-REFERENCE TO RELATED APPLICATIONS

This application is a continuation application of U.S. Utility patent application Ser. No. 17/015,992 entitled "KNOTLESS ANCHOR," filed Sep. 9, 2020, which is a continuation application of U.S. Utility patent application Ser. No. 16/021,423 entitled "KNOTLESS ANCHOR," filed Jun. 28, 2018, which claims the benefit of U.S. Provisional Patent Application Ser. No. 62/541,286 entitled "KNOTLESS ANCHOR," filed Aug. 4, 2017, the disclosures of which are each incorporated by reference herein in their entireties.

TECHNICAL FIELD

The invention relates to improved orthopedic tools and methods for use during orthopedic surgical procedures, including joint repair and/or replacement procedures. More specifically, disclosed are improved methods, apparatus and/or systems for securing and/or anchoring tissue structures to bones with a durable securement that facilitates accuracy and predictability of joint tension during joint surgery, including orthopedic repair of rotator cuff injuries.

BACKGROUND OF THE INVENTION

There are a wide variety of suture anchor designs, related devices and/or surgical techniques for securing sutures, which can be passed through soft tissue, to bone. Many of such designs rely on the interference between external features of the anchor (i.e., barbs, ribs, ridges, etc.) and the bony inner surface of the fixation hole to provide fixation strength. Where there is a high amount of interference required, this may require a tighter fit between the anchor and the hole, resulting in a large force required to insert the anchor into the bone—which can result in broken anchors, broken insertion tools, damage to the suture and/or damage to the bone itself.

Another important aspect in the placing of suture anchors is ensuring that the suture is properly positioned with a desired tension to pull the captured tissue into intimate contact with the bone (and/or with some other location). Many anchors will allow the suture tension to change an unintended amount during deployment of the anchor, which typically requires the surgeon to estimate and/or anticipate how suture tension might change during the various anchor installations steps, including final placement of the anchor in the bone. Improper tensioning of the suture can result in under- or over-tensioning of the tissue against the bone. In addition, once a desired suture tension has been achieved or "set" with an anchor, it is often difficult to loosen, tighten or otherwise alter the suture tension in the anchor without damaging the suture, the bone and/or requiring at least some removal of the anchor from the bony anatomy.

Another important feature of suture anchoring relates to suture securement—i.e., how the suture is secured to the anchor and/or the bone. In many cases, the final step of securing a suture and tissue is to tie a knot in the suture-which has been shown to be a common source of anchor/suture failure. Not only can tying a tensioned suture be difficult to accomplish (especially without altering the suture tension before, during and/or after the tying process), but suture tying typically requires a great deal of practice and skill by the surgeon and takes up a significant amount of time during the surgical procedure itself.

Since knots and knot tying are often problematic, several knotless suture anchor designs have been developed. For example, the Bioknotless™ anchor by DePuy Mitek is an anchor that is loaded with a loop of suture secured to the anchor with a knot. The loop is passed through the tissue, then the loop must be hooked in a groove at the tip of the anchor. This step can be tedious and difficult, depending on the angle of approach to the hole. Finally, the anchor is tapped into the hole in the bone. The final tension on the suture loop and attached tissue is controlled by the anchor insertion depth. This requires the surgeon to drill a hole deep enough to achieve sufficient tension. If the bite of tissue through which the suture is passed is smaller than expected or achievable, the anchor may reach the bottom of the hole before enough tension is placed on the tissue. This results in the tissue not being pulled firmly against the bone surface and may result in inferior long-term repair strength. Depending on the angle of approach and the location on the bone (such as inferior on the glenoid), it may be impossible to drill a deep enough hole to achieve the desired tension.

Arthrocare has developed the LabraLock P™ anchor, which is a two-part anchor made from PEEK (Polyether-ether-ketone), which secures two strands of suture (the strands which form the loop that is passed through the tissue) between the anchor and the bone, and the other two strands (the free ends of suture) between the anchor's inner shaft and the outer, tube portion. The outer tube portion has barbs which secure the anchor in the bone via an interference fit.

The PushLock™ anchor, by Arthrex, is also a two-part anchor. The tip of this anchor has an eyelet through which the suture legs are loaded. This tip is placed at the bottom of a hole drilled into the bone. At this point, the surgeon may adjust the tension on the suture, thereby pulling the tissue closer to the surface of the bone. When the tension is deemed correct, the rear portion of the anchor is driven into the hole. This rear portion is a length of tube which has circumferential barbs on its outer diameter which provide interference to anchor the device in the hole. Since the barbed portion of the anchor is a full cylinder, it can require a great deal of force to insert into a smaller diameter hole, especially in hard bone. Moreover, since the suture is tensioned all at once, without any engagement with the hole when the rear portion of the anchor is driven into the hole, the final tension may not be correct. Once the rear portion of the anchor is in the hole, the suture tension cannot be adjusted.

The ConMed Ultrafix Knotless Minimite™ anchor is a knotless anchor made of metal, which many surgeons are hesitant to deploy within a joint. If this anchor design were to pull out of the bone, the metal could cause a great deal of damage rubbing against the articular surfaces—e.g. the humeral head and glenoid.

Smith & Nephew has marketed the KINSA™ suture anchor. It is a knotless design made of PEEK which is tapped into a pre-drilled hole in the bone. The anchor is preloaded with suture tied in a one-way sliding knot within the anchor body, which allows the surgeon to adjust the tension after the anchor has been deployed. This anchor cannot utilize suture that is already passed through tissue and only can provide a simple stitch in the tissue.

The POPLOK™ by Conmed Linvatec is another knotless anchor. It is a two-piece polymer anchor that has the ability of accepting and tensioning the suture individually prior to locking the suture to the anchor. However, this anchor has multiple pieces that can fail.

The VERSALOK™ by Mitek is also a knotless anchor. It is a two piece polymer and metal design that has the ability of accepting and tensioning the suture individually prior to locking the suture to the anchor. It also has multiple parts forming the anchor and the inner member is metallic.

The CUFFLINK™ Knotless and CUFFLINK SP™ Knotless suture (self-punching with metal tip) anchors, also marketed by Mitek, are fabricated of PEEK, using a one-piece polymer design without the employment of any metal. The design allows the anchor to accept more than two suture ends, and each of these ends can be tensioned or have tension released individually by hand, prior to final anchor deployment, providing the surgeon the ability to achieve the desired tension on each suture. The anchor may also accept tissue (such as a tendon, ligament, xenograft, allograft, or collagen scaffold) with or without suture, enabling a direct tissue to bone repair. The metal tip version allows the anchor to be malleted directly into the bone without the need for a pilot hole. Finally, the design incorporates a metal deployment device to provide strength to the anchor during deployment, thereby reducing breaking of the anchor.

Many of these existing knotless anchors and associated deployment tools incorporate multiple moving and interacting parts that require very tight tolerances in component manufacturing, which can significantly increase the expense and difficulty of device manufacture and assembly, and often negatively impact reliability of the anchor and related delivery systems. Moreover, existing anchor designs do not facilitate "unlocking" of a suture out of one or more locking slots-such actions may not be possible with some designs, and with other designs unlocking may require an additional surgical tool and/or additional assistance from another surgeon or assistant. In addition, many knotless anchors "over- or under-tension" the suture or tape when the anchor is being fully seated in the bone, and such designs do not have any provision for unlocking and/or adjusting tension of the suture or tape after the anchor is fully implanted.

BRIEF SUMMARY OF THE INVENTION

The various inventions disclosed herein include the realization of a need for an improved suture anchor, system components and deployment tools, and related surgical methods for placing one or more anchoring sutures within a bone or other tissue structure. More specifically, the various suture anchors disclosed herein provide durable suture fixation employing multiple points of securement and/or fixation, do not solely rely upon compression between the anchor and bony surfaces of the fixation hole for suture locking, and provide for suture "release" and/or modification of suture tension (i.e., increase and/or decrease) and/or length after initial placement and "locking" of the suture within the suture anchor and/or placement of some or all of the anchor into the bone. Moreover, many of the embodiments disclosed herein allow a physician to optimize placement and final tensioning of the suture before the anchor is fully seated within the bone, with the suture tension/length remaining constant while the anchor is fully seated (i.e., by malleting) into the bone. Various embodiments may also allow the physician to alter suture tension and/or positioning to varying degrees after the anchor has been fully seated into the bone.

By allowing a physician to achieve an optimal suture tension and/or positioning before the anchor is fully seated within the bone (which is desirably unaltered during the seating process), and by further allowing the physician to freely lock and/or unlock the suture from the suture anchor to alter suture tension and/or length/positioning, the present invention greatly improves the accuracy and predictability of joint tension and tissue positioning during joint surgery, which can significantly improve surgical outcomes as well as significantly reduce required operative time.

In various embodiments, a knotless anchor implant and associated system components are described which incorporate an internal dual suture locking mechanism that includes a pair of longitudinally-extending adverse oblique slits, with an associated delivery device comprising a cannulated delivery tool with handle and an internally sliding shaft section that desirably limits, blocks and/or otherwise inhibits the locking mechanism from "fully" engaging at various points during a surgical procedure, which also can include selected unlocking or partial-unlocking of some or all of the suture locking mechanism, if desired, by the surgeon.

In various embodiments, a suture anchor can include at least one suture opening that can be sized and configured to accommodate one or a plurality of sutures and/or suture tapes within a single anchor (although multiple suture openings with associated locking slots are contemplated in alternative embodiments herein). If desired, the anchor could alternatively include suitable features to accommodate other anchoring or connecting materials, including surgical wires, flexible ties, bands, and/or the like.

The present disclosure describes a suture or tissue anchor and associated deployment tools that are intended to secure suture or tissue to bone. There are many soft tissue to bone repair procedures, such as rotator cuff, SLAP (Superior Labral tear from Anterior to Posterior), and Bankart lesion repairs, or reconstruction of labral tissue to the glenoid rim, in which a surgeon needs to secure tissue in close contact with bone. Often the bone surface is roughened, and when tissue is pulled into intimate contact, the body's healing response will fuse the tissue and bone together. This suture is then passed through the soft tissue at the desired location, and the suture is secured to the anchor by tying a knot. Other methods include passing suture through the tissue first and then fastening the anchor and suture to the bone without knots.

Even more particularly, there are provided in various aspects of the present invention an anchoring system for securing tissue to bone, which comprises an implant having a body which includes a suture eyelet extending transversely therethrough, and suture recesses and one or more pinch slits extending along a portion of a length of the body, each recess/slit having a predetermined angle relative to a longitudinal axis of the anchor, the recesses/slits desirably being nonparallel to the longitudinal axis, being non-parallel to one or more suture slots and/or and in various embodiments non-parallel to each other.

According to at least one exemplary embodiment, a suture anchor may include a externally ribbed portion, the externally ribbed portion including a body, the body having a tip and a base with a generally transverse opening extending through the body, the opening configured to receive one or more suture threads or tapes, the opening including at least one posterior locking slot and/or slit in communication with the opening, the posterior locking slot/slit extending oblique to the longitudinal axis of the body. At least one of the ribs on the ribbed body including a ribbed section and an interrupted section, with at least a first portion of the posterior locking slit extending along the interrupted section and at least a second portion of the posterior locking slit extending along the ribbed section.

In various aspects of the invention, there are disclosed methods for securing soft tissue to bone, which can comprise steps of driving an implantable anchor having a body distally into a desired bone site using an insertion device to a predetermined initial deployment depth, and applying pressure to suture or tissue disposed between the anchor body and adjacent bone, using a recess disposed on an outer surface of the body and a wedging or pinch ramp also disposed on the outer surface of the body, proximal to the suture recess. Additional steps can include tensioning free ends of the suture or tissue disposed between the anchor body and adjacent bone to a desired level, partially and/or fully withdrawing a blocking mechanism and provisionally locking one or more sutures within the anchor, and driving the implantable anchor a further distance distally into the bone site to fully lock the suture within the anchor. The suture or tape can be wedged and/or pinched between one or more barbs on an outer surface of the implant body and adjacent bone and also between features of each slit in the anchor body to lock the suture in place. Further method steps can include rotating the anchor to engage the suture between additional barbs on the outer surface of the implant body and adjacent bone, and/or fully withdrawing the blocking mechanism from the handle and/or releasing the insertion device from the anchor, and trimming the free suture ends to complete the procedure.

BRIEF DESCRIPTION OF THE SEVERAL VIEWS OF THE DRAWINGS

FIGS. 11A through 11D depict exemplary positioning of a suture and associated suture grooves in the ribs of a suture anchor;

DETAILED DESCRIPTION OF THE INVENTION

Figure 1A:
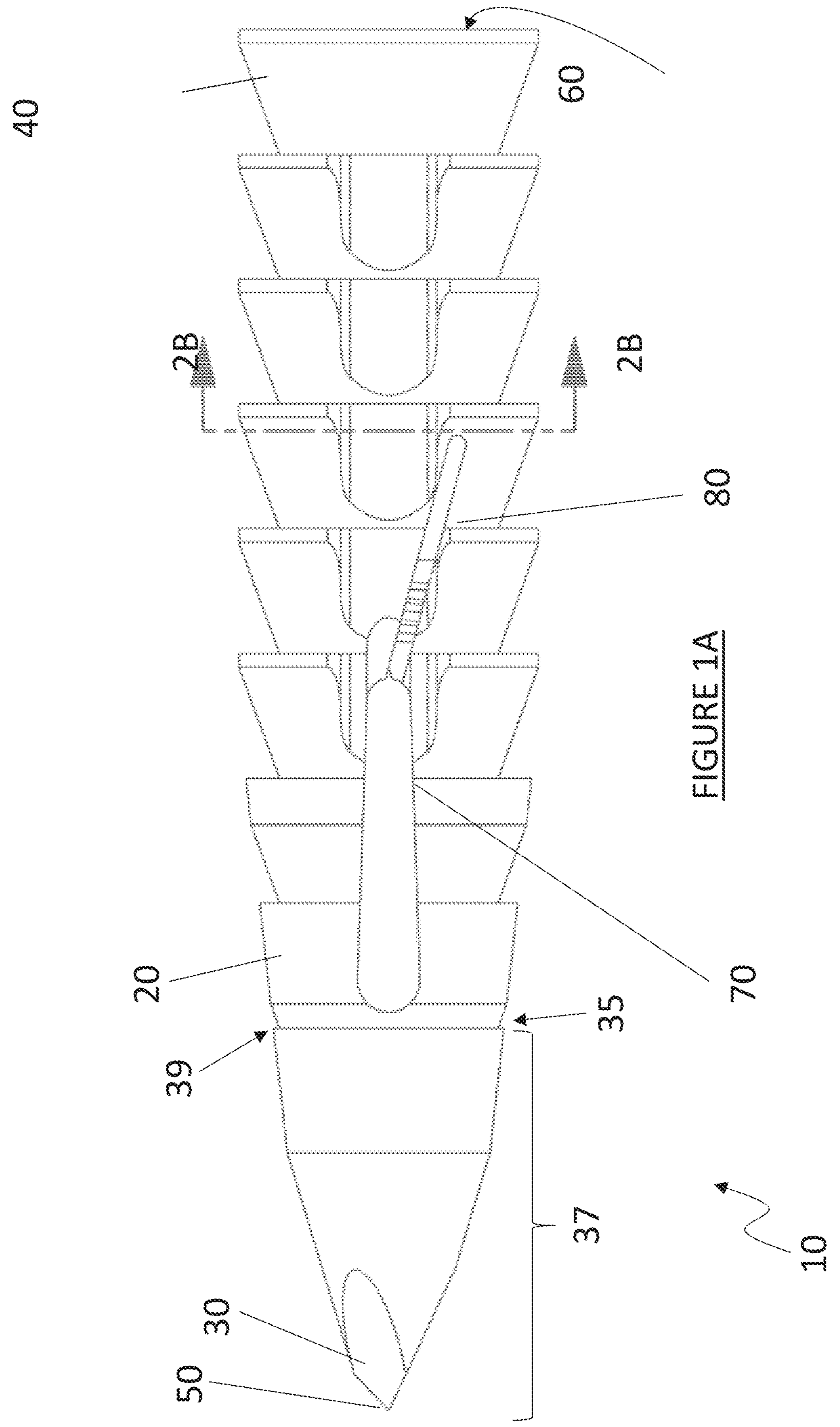
FIG. 1A depicts a side plan view of one exemplary embodiment of a suture anchor.

The disclosures of the various embodiments described herein are provided with sufficient specificity to meet statutory requirements, but these descriptions are not necessarily intended to limit the scope of the claims. The claimed subject matter may be embodied in a wide variety of other ways, may include different steps or elements, and may be used in conjunction with other technologies, including past, present and/or future developments. The descriptions provided herein should not be interpreted as implying any particular order or arrangement among or between various steps or elements except when the order of individual steps or arrangement of elements is explicitly described.

Disclosed herein are a variety of simple-to-insert suture anchors and associated deployment tools which allow for adjustment of suture or tissue tension prior to deployment, do not change the tension on the suture or tissue (and as a result, the captured tissue) when the anchor is deployed, do not require a knot to secure the suture or tissue, accepts multiple suture ends and provides for fine and/or gross adjustment of suture tension and/or positioning at virtually any point during the surgical procedure.

The various systems and devices described herein include the design and manufacturing of suture anchors and related tools having various pre-defined shapes, sizes, widths, spans, thicknesses and/or contours which could be provided in kits of one or more implants of various standard shapes and/or sizes, or could be based, at least partially, off of anatomical shape image information obtained from one or more pre-operative scans (i.e., x-ray, sonogram, CT scan, MRI, etc.) of the patient's anatomy. In such case, the anatomical image information could be identified, scanned, processed and/or analyzed, and a particular implant size, shape, length and/or other features (or a series of implants within a range of sizes, shapes, lengths and/or other features) could be designed and/or selected (i.e., from a library of pre-existing designs and/or from a stockpile of previously manufactured implant components) for use with the patient.

Various embodiments described herein can be used in conjunction with patient specific devices and/or tools that have been constructed specifically for an individual patient, including devices that accommodate the contours and/or dimensions of the patient's bony surfaces and/or other anatomy. The shape of such anatomy can be determined from scans or digital images like a CT Scan or a MRI, and in many cases, such scans can help the surgeon determine an ideal position for cutting and/or preparing anatomical structures for receiving implant components.

If desired, the various suture anchors and/or related tools described herein could be designed and/or manufactured using traditional implant manufacturing techniques, or the various implants and/or components (or portions thereof) could be created using 3D manufacturing techniques (i.e., could be 3D printed using various materials). Such 3D manufacturing techniques could include "just in time" manufacturing in the hospital and/or operating room, if desired, as well as manufacture of multiple copies and/or sizes of suture anchors as needed and/or anticipated.

The various devices, systems and methods disclosed herein comprise a simple-to-insert suture anchor which allows adjustment of suture or tissue tension prior to and/or after deployment, does not change the tension on the suture or tissue (and as a result, the captured tissue) when it is deployed, does not require a knot to secure the suture or tissue, and accepts multiple suture ends.

Figure 1B:
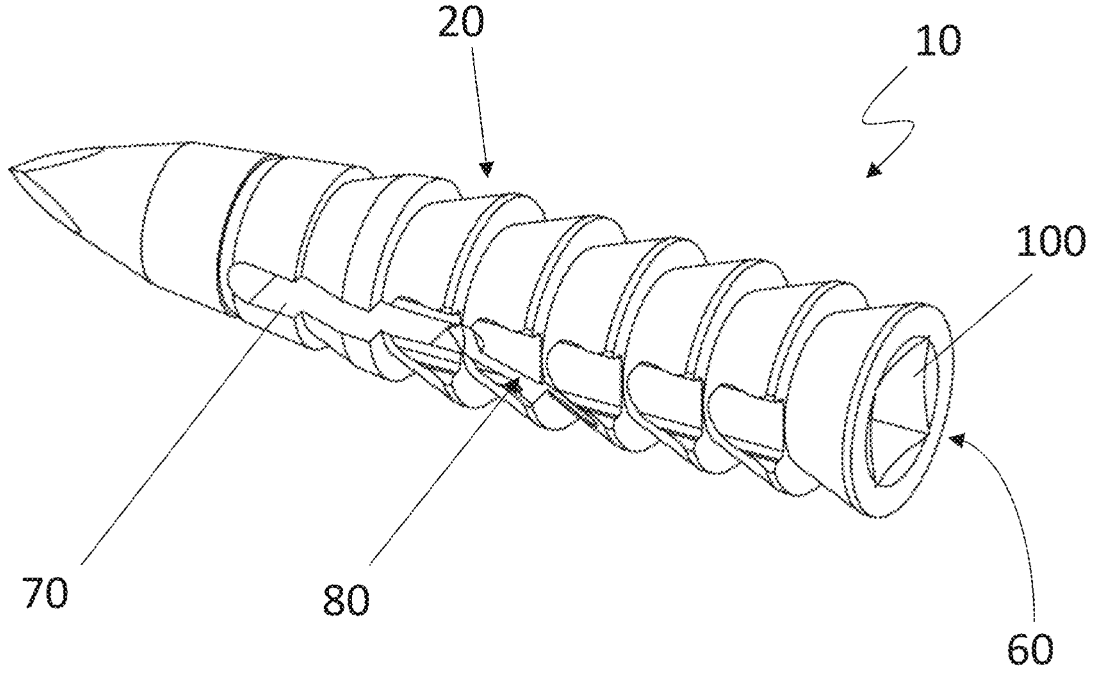
FIG. 1B depicts a perspective view of the suture anchor of FIG. 1A.

FIGS. 1A and 1B depict side and perspective views, respectively, of one exemplary embodiment of a suture anchor 10. In this embodiment. The anchor comprises a generally cylindrical body 20 having a front or proximal end 30 and a back or distal end 40, the proximal end 30 having a reduced diameter or pointed tip 50, and the distal end including a relatively flat section. An opening or tunnel 60 extends from the distal end 40 into the cylindrical body 20, which in various embodiments can extend fully from the proximal end to the distal end of the body. A suture eyelet or slot 70 extends in a generally transverse direction through the body, the slot forming an opening to accommodate a suture or tape (not shown) therethrough. A pair of locking slits 80 can formed in the body 20, the locking slits extending in a generally posterior direction from the slot 70, the locking slots desirably including a reduced width portion or suture cleat (i.e., adjacent to the suture pinch slits) which can wedge, grip and/or otherwise secure the suture to the anchor in a known manner. Desirably, the slot 70 and the locking slits 80 are in communication with the tunnel 60 in the body 20.

In various embodiments, the suture slot or slots can comprise elongated rectangular or trapezoidal shapes, optionally with rounded corners, and the length of one or more of the slots can extend approximately 4.5 mm or greater (or could be shorter in other embodiments, if desired) along the longitudinal axis of the anchor, which length can allow for a larger number and/or size of suture or suture tape to be inserted into the slot without "bunching," folding, twisting and/or clogging up the slot. For example, a newer trend in rotator cuff repair is the use of 2 mm suture tapes to hold down a repair using a knotless anchor, and multiple strands of these larger suture tapes can be easily accommodated by the currently disclosed design.

Unlike older anchor slot designs, which are primarily designed to accommodate rounded and/or oval sutures, various of the slot designs and/or configurations in Applicant's disclosed embodiments can be elongated to accommodate the relatively wider and flatter cross-sections of suture tape, allowing the tensioned suture tape to maintain a flatter profile within the slot and/or locking slits, which contributes greatly to maintenance of the suture's structure and integrity during and after the surgical procedure. The elongated slot design also desirably permits multiple thinner tapes to "lay flat" on top of each other within a single slot, instead of jamming as many sutures as possible with a single hole (which was often an objective of prior art designs). In various embodiments, a 4.5 mm long slot in an anchor can accommodate a wide variety of suture tape sizes, including 2, 2.5, 3 and/or 3.5 mm wide suture tapes, with the disclosed design allowing the tape to lay flat within the slot, as well as properly enter and/or maintain a proper alignment within the locking slit(s) when locking of the suture tape is desired. In addition, proper orientation of the flat, wide suture tape can contribute greatly to the surgical repair, as the flat wide tape can hold the tendon optimally to the bone (in various surgeries) and the size and orientation of the tape holding the repair can be one of the most important considerations contributing to a successful surgery. In various preferred embodiments, the elongate slot can extend 20% or more of the length of the anchor (i.e., a 4.5 mm slot in a 22 mm anchor is 20.5% of the anchor length), while in other embodiments the elongated slot could range from 15% to 30% of the anchor length, while in still other embodiments the elongated slot could range from 20% to 45% of the anchor length.

As best seen in FIGS. 1A and 1B, in one embodiment of the anchor can include a generally smooth proximal portion 37 positioned at the proximal end 30 of the anchor 10, with a first proximal groove 35 located at a distal end 39 of this smooth proximal portion 37. This design can desirably facilitate the proper placement of the anchor into a pilot hole in the bone (not shown) by the surgeon, which can desirably be accomplished without fully engaging the proximal groove 35 into the surrounding bone of the pilot hole. Such an arrangement desirably gives the surgeon the option to insert and remove the anchor, and find a desired anchor placement and/or orientation, without engaging or damaging the pilot hole and/or the anchor. In addition, the surgeon can twist the anchor within the pilot hole to find a proper placement of the anchor and suture relative to the cuff. Once proper positioning and/or orientation has been attained, the surgeon can impact the anchor into the bone to engage one or more ribs of the anchor. In one exemplary embodiment, the first proximal groove 35 can be located approximately 8 mm from the distal end 39 of the anchor, and/or the first proximal groove 35 can be positioned approximately 14 mm from the proximal end 30 of the anchor 10.

Figure 2A:
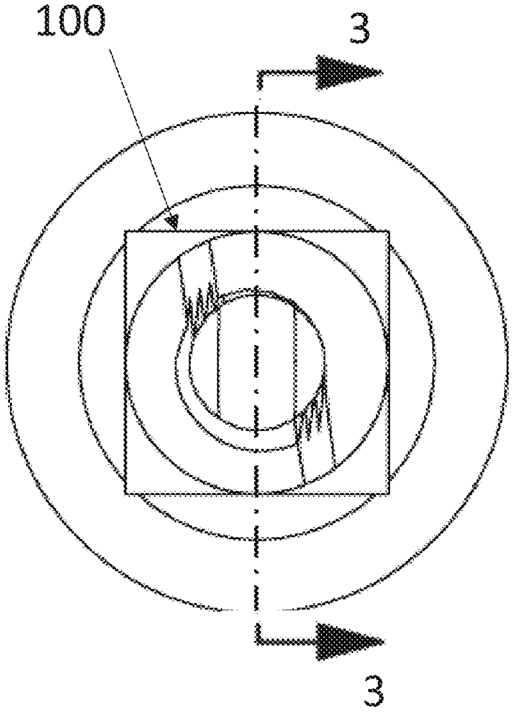
FIG. 2A depicts another side view of the suture anchor of FIG. 1A.
Figure 2B:
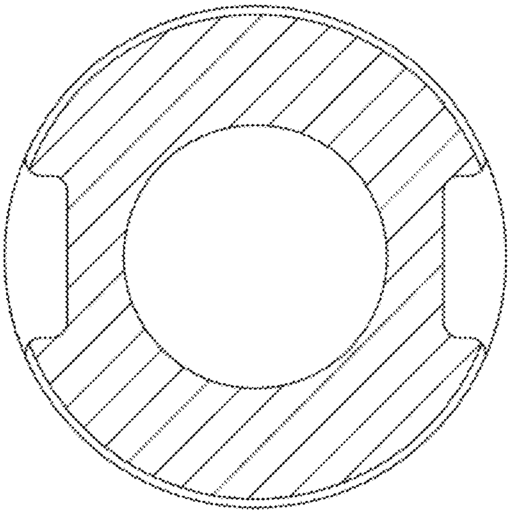
FIG. 2B depicts a cross-sectional view of the suture anchor of FIG. 2A taken along line 3-3.
Figure 3:
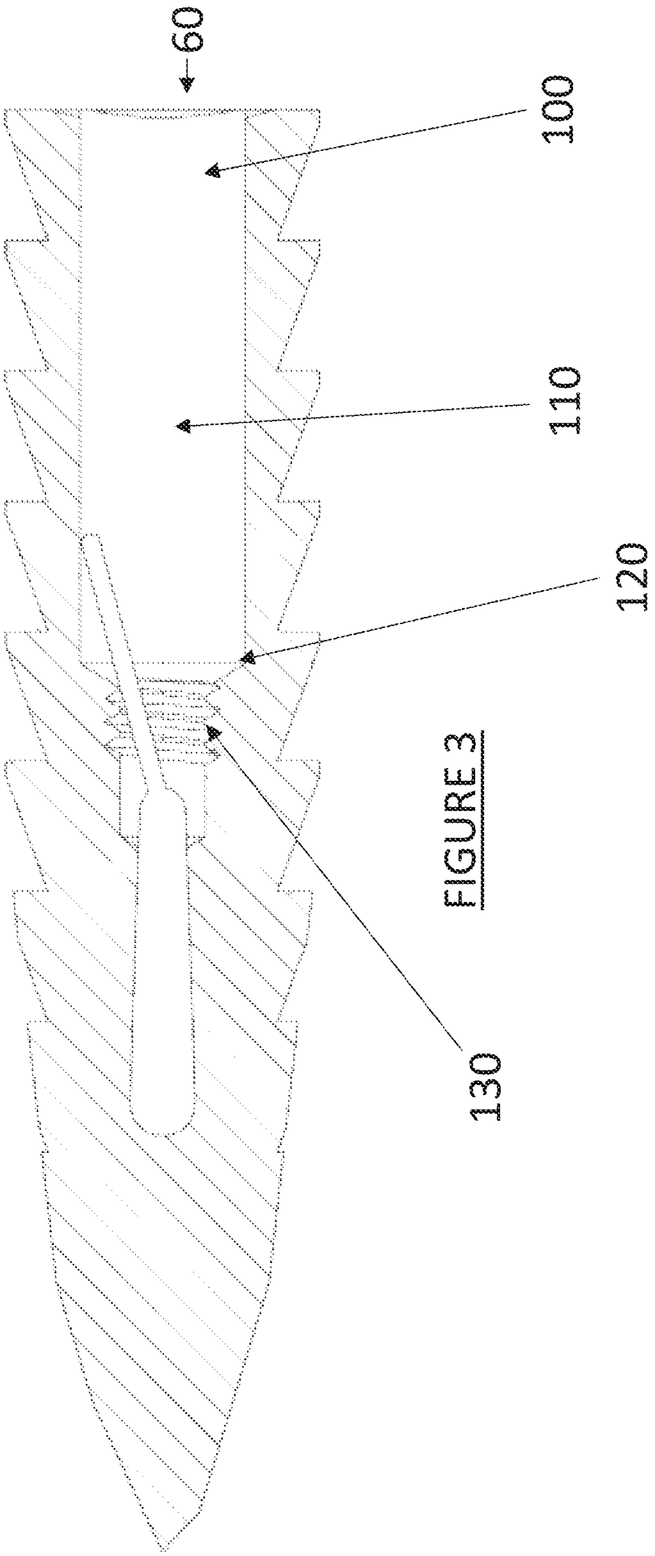
FIG. 3 depicts a cross-sectional side view of the suture anchor of FIG. 1A.

As best seen in FIGS. 1B and 2A, the tunnel 60 can include a drive portion 100, the drive portion incorporating an outer shape (in this instance, a square or hexagonal shaped opening) that can optionally be engaged with a corresponding shape (i.e., a square or hexagonal shaped driver) on a placement tool (not shown), which desirably allows a physician to advance and/or rotate the implant 10 a desired amount during the surgical procedure. Located forward of the drive portion 100 (see FIG. 3), the tunnel can include a tubular section 110, which can be of virtually any shape (including the same or different shape as the drive portion), which in some embodiments desirably corresponds to a cylindrical (or other) shaped portion of the placement tool (not shown). If desired, the tubular section 100 can further include a necked-down portion 120, which is positioned proximate to an internally threaded portion 130 of the tunnel 60, which is desirably engageable with a corresponding externally threaded section of the "locking and/or blocking piece," to be described later.

Figure 4A:
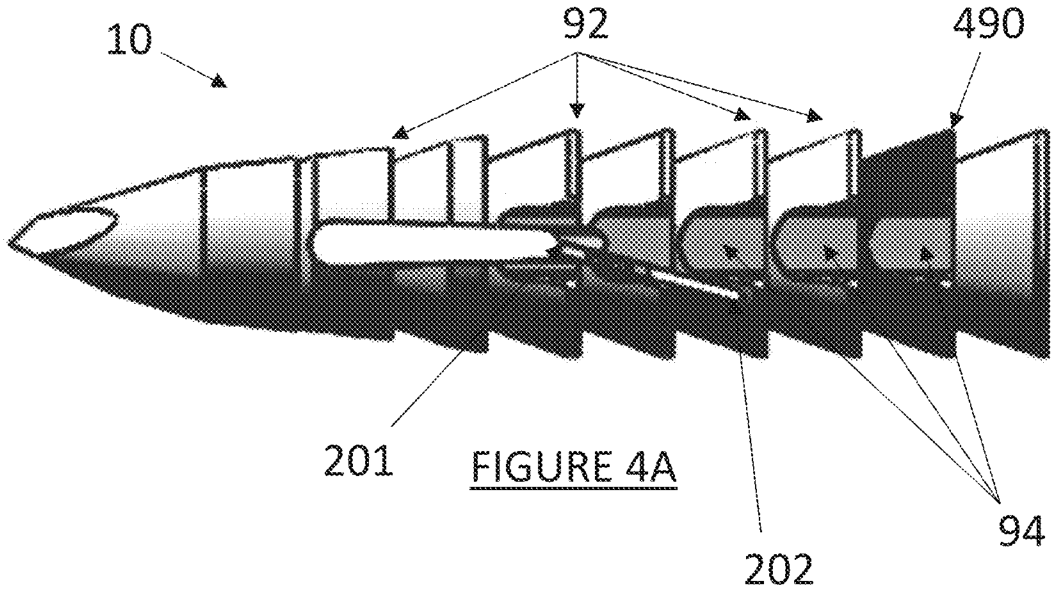
FIGS. 4A and 4B depict side and top plans views of the suture anchor of FIG. 1A.
Figure 4B:
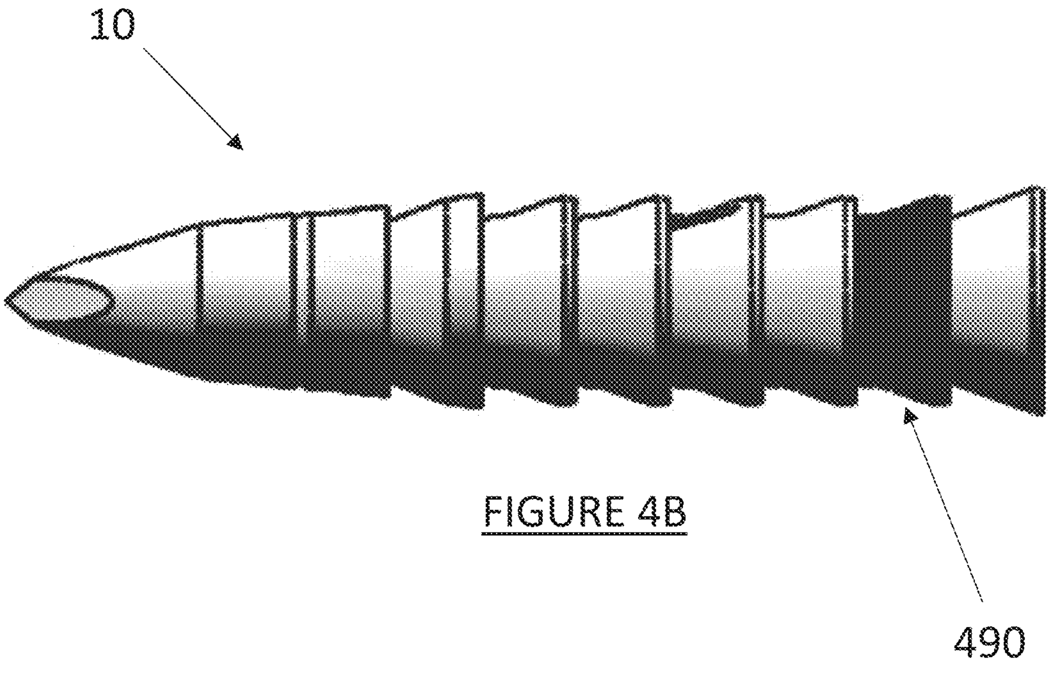

In various embodiments, the suture anchor can comprise external surface features for securing the implant within surrounding bone. These external surface features can comprise ribs, bone barbs, threads, projections and/or similar features. If desired, suture ribs and/or barbs could be disposed on the outer surface of the body at proximal and/or distal end(s) thereof, for clamping suture or tissue between the outer surface of the body and adjacent bone. If desired, bone displacement tabs could be disposed on a proximal and/or distal portion of the implant body, for displacing bone distal to suture for allowing optimal suture sliding during initial deployment of the anchor. As best seen in FIGS. 4A and 4B, the suture anchor 100 can include a series of ribs 92 or other externally facing projections that desirably serve to retain the anchor within the bony anatomy in a known manner (and/or which can secure and/or "wedge" the suture in a desired position between the ribs and the surrounding bony anatomy), with a suture recess or grooved section 94 formed into the anchor ribs 92 (which can include a pair of grooves formed in opposing sides of the anchor).

Figure 5:
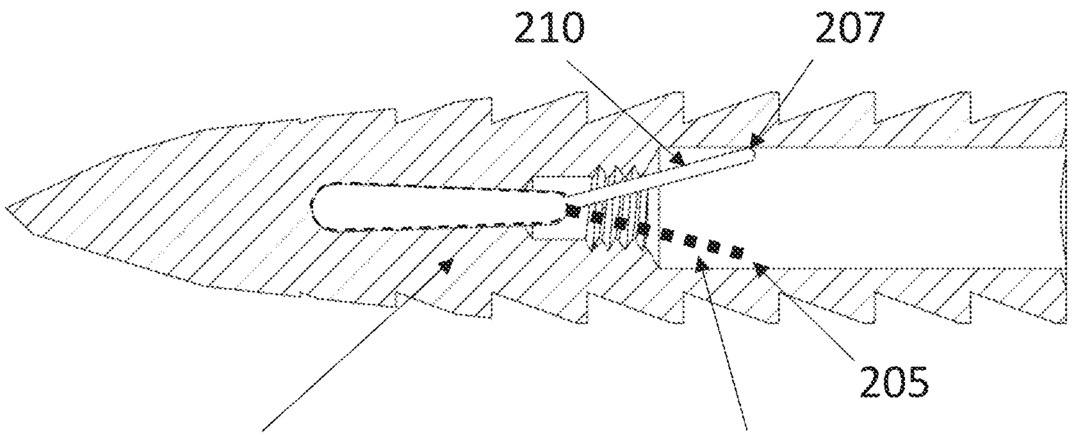
FIG. 5 depicts a cross-sectional side view of the suture anchor of FIG. 1A, with an additional suture slot position shown in dotted line.
Figure 6A:
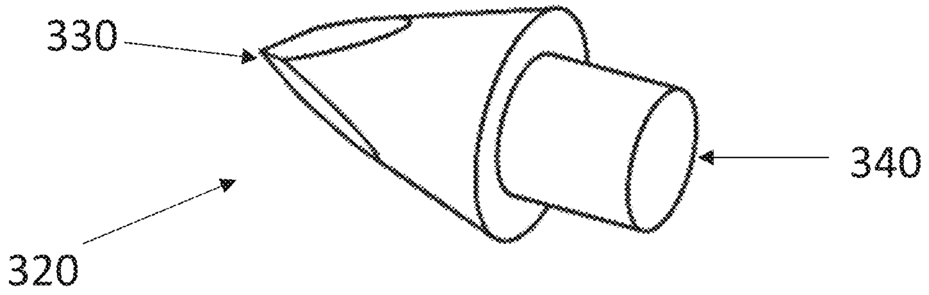
FIGS. 6A through 6D depict various views of one exemplary embodiment of an anchor tip.
Figure 6B:
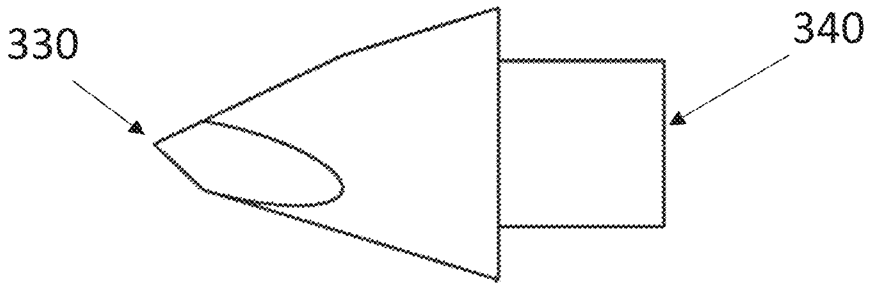
Figure 6C:
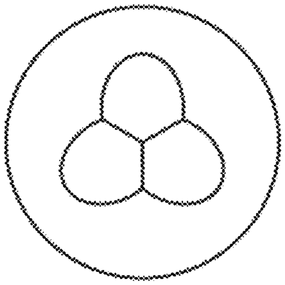
Figure 6D:
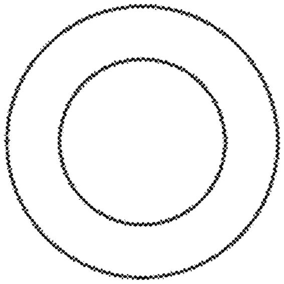
Figure 7A:
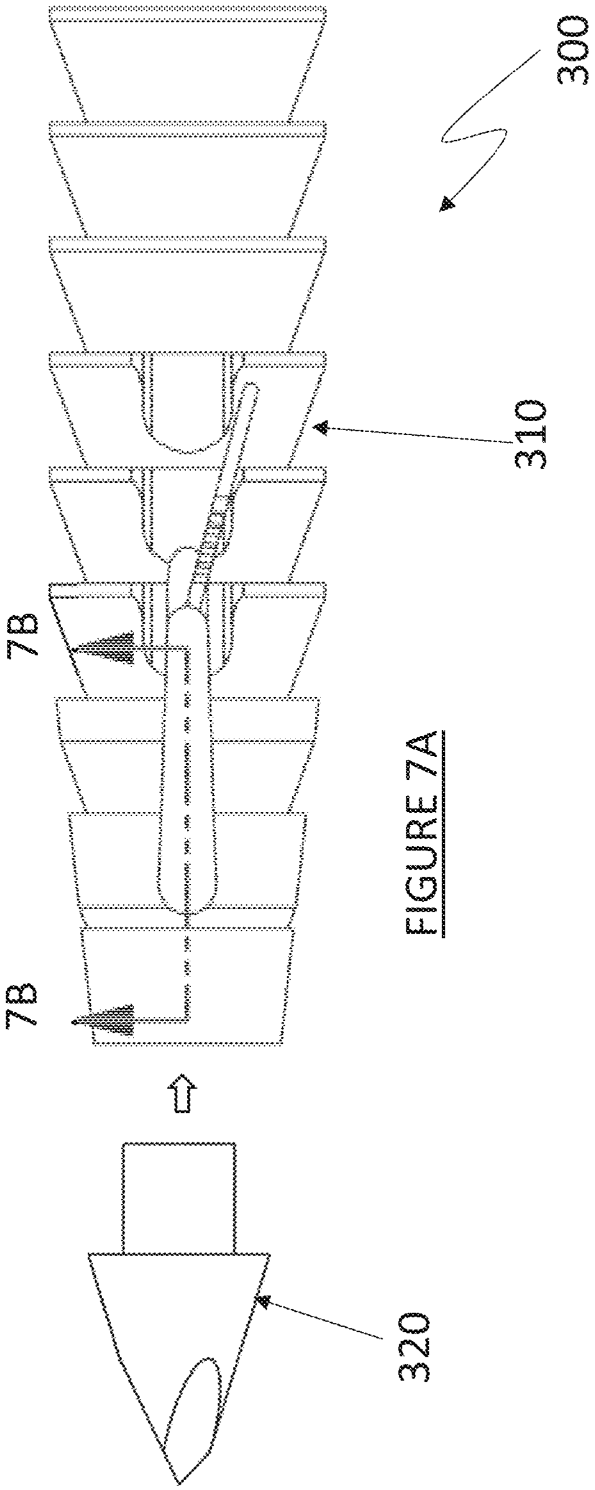
FIGS. 7A and 7B depict various views of the anchor tip of FIGS. 6A through 6D being attached to another exemplary embodiment of a suture anchor.
Figure 7B:
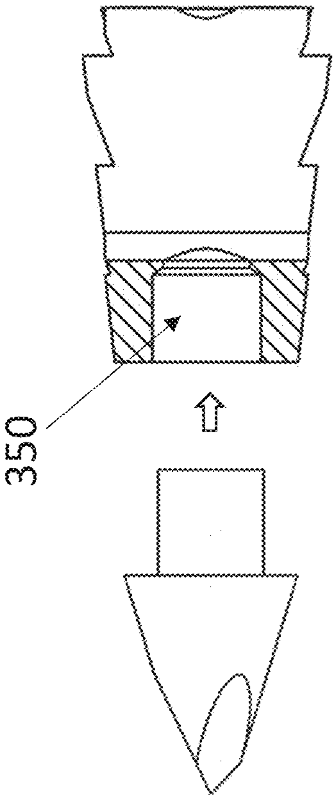

As best seen in FIG. 5, the body 20 can include one or more suture pinch slits, such as a first locking slit 200 and a second locking slit 210, the first and second locking slits extending through opposing sides of the body 20 and optionally terminating in proximal pinch cleats 205 and 207. In various embodiments, the locking slits can be “angled” or tilted relative to the longitudinal axis of the anchor, which in various embodiments can include a slit 200 having a distal end 201 that can be positioned within the grooved section 94 and a proximal end 202 that can be positioned outside of the grooved section 94 (see FIG. 4A).

In various embodiments, the locking slits 200 and 210 will desirably be positioned in a non-parallel arrangement, such that the first locking slit 200 and second locking slit 210 do not align with each other when viewed from a side of the implant 10 (see FIG. 4A). While FIG. 5 depicts the locking slits in equal and opposing configurations (i.e., both of which are depicted as being slanted approximately 15 degrees from the longitudinal axis of the body 20), in various alternative embodiments the locking slits could be positioned at differing angles from the longitudinal axis and/or from each other, including a potential for one slit to be positioned parallel to the longitudinal axis with the other slit being angled some number of degrees or portions thereof away from the longitudinal axis. In various other embodiments, the locking slits could be of differing sizes, shapes, widths and/or lengths, if desired, which could include curved and/or angled (i.e., “V” shaped) locking slit designs. In various embodiments, one or both of the locking slits could be angled approximately 5, 6, 7, 8, 9, 10, 11, 12, 13, 14, 15, 16, 17, 18, 19, 20, 21, 22, 23, 24, 25, 26, 27, 28, 29 or 30 degrees from the longitudinal axis, or each locking slit could be positioned at virtually any combination thereof. In at least one exemplary embodiment, the locking slits could be angled from 12 to 18 degrees from the longitudinal axis, at the same or differing angles, while in other embodiments, the locking slits could be angled from 10 to 20 degrees from the longitudinal axis, at the same or differing angles, while in still other embodiments, the locking slits could be angled from 7 to 23 degrees from the longitudinal axis, at the same or differing angles. In other embodiments, the one or more slits could be positioned at one or more obtuse angles (i.e., more than 90 degrees but less than 180 degrees) relative to the elongated slot(s), with each of the locking slits positioned at a same or a different obtuse angle, depending upon a desire anchor and/or locking performance.

In various embodiments, the engaging components of the locking slits can extend along a constant depth within the anchor, while in other embodiments the engaging components of the locking slits could be ramped inward and/or outward from the center of the anchor, including a constant and/or varying slopes extending towards the rearward surface of the suture anchor.

In various embodiments, the anchor (and optionally various portions of the associated deployment tools) may comprise PEEK (PolyEther-Ether-Ketone) or other materials commonly used in constructing surgical implant components, which can desirably withstand the various forces of being impacted and/or tapped into bone during various surgical procedures. In various embodiments, the anchor could comprise a one-piece suture anchor with an associated non-disposable two-piece handle and delivery assembly (to be described later), or in alternative embodiments some or all of the various components of the delivery assembly thereof could be disposable. Desirably, some or all of the suture anchor structure will be radiolucent, non-metallic and/or allow the use of various non-invasive imaging techniques.

In at least one alternative embodiment, best seen in FIGS. 6A through 6D, 7A and 7D, a suture anchor 300 can be constructed that includes a PEEK body 310 with an associated metal proximal tip 320. The tip 320 can include a pointed or proximal end 330, with a cylindrical shaft of plug 340 positioned on a distal end. For use, the plug 340 can be inserted into a corresponding opening 350 in the anchor 300, which could optionally include a press-fit or other arrangement between the components. In use, the metal tip 320 will desirably strengthen the anchor and/or anchor tip, as well as potentially provide a sharpened cutting/pointed surface to improve bone penetration by the anchor. If desired, the optional metal tip may allow for the anchor to be inserted directly into bone without the requirement of a pilot hole. In various embodiments, the metal tip 320 could optionally be separable from the remainder of the suture anchor 300, such that if the anchor failed and “pulled out” of the bone for some reason, the metal tip 320 might remain imbedded in the bone and thereby potentially avoid causing any contact or rubbing damage against body surfaces such as the articular surfaces—e.g. the humeral head and/or glenoid.

Figure 8A:
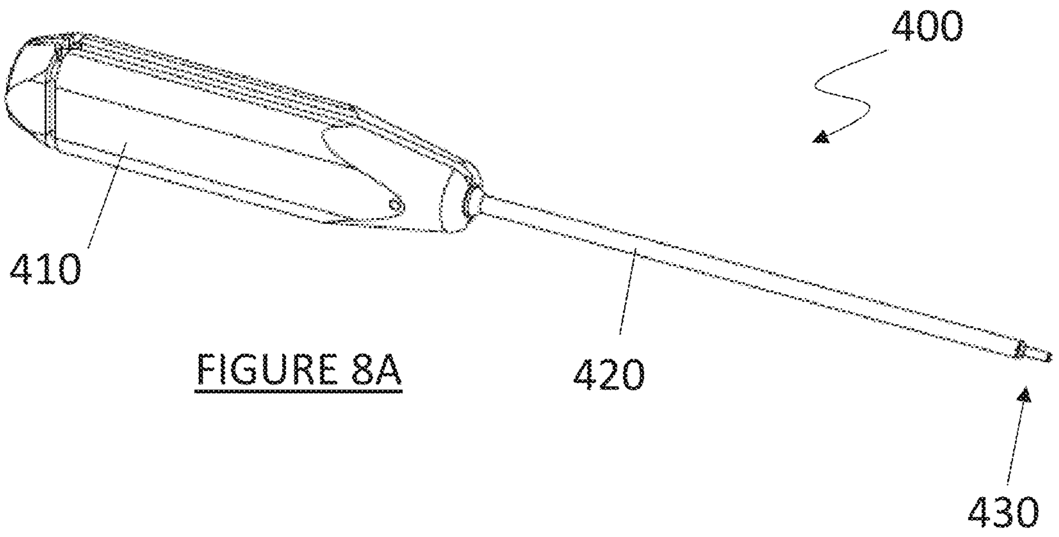
FIGS. 8A through 8D depict one exemplary embodiment of an insertion and deployment tool for use with the various suture anchors described herein.
Figure 8B:
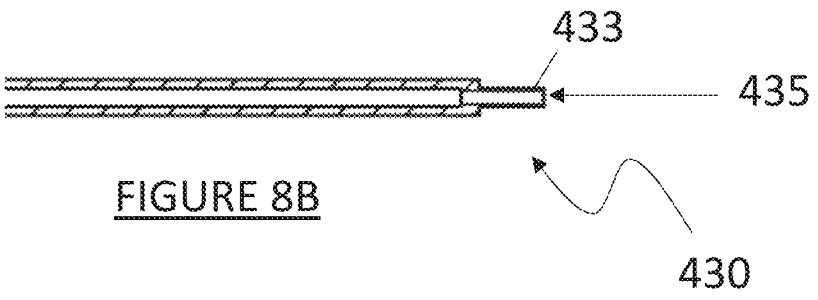
Figure 8C:
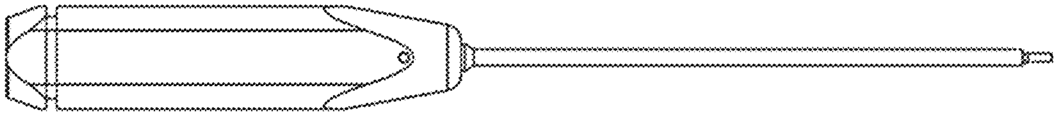
Figure 8D:
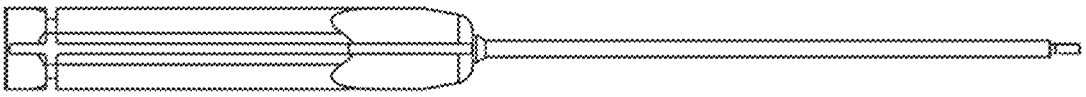
Figure 9A:
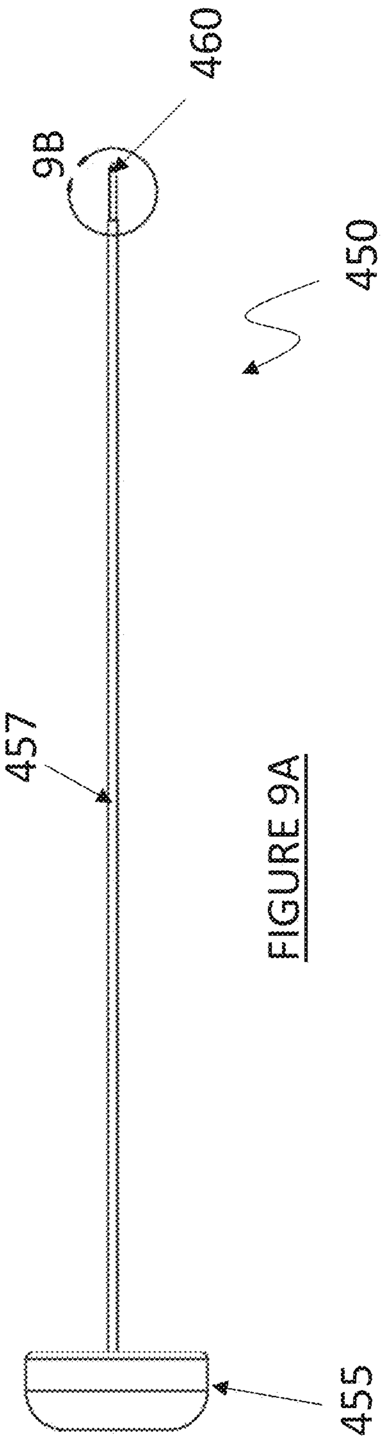
FIGS. 9A and 9B depict various views of one exemplary embodiment of an inner shaft tool for use with the insertion and deployment tool of FIGS. 8A through 8D.
Figure 9B:
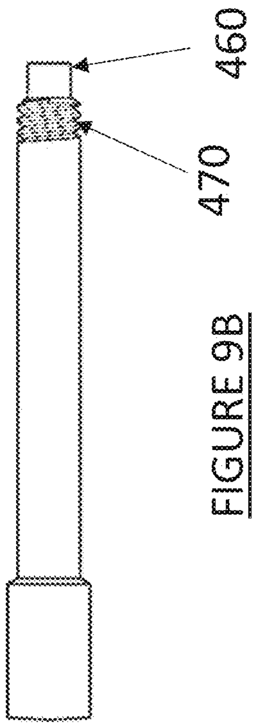
Figure 10:
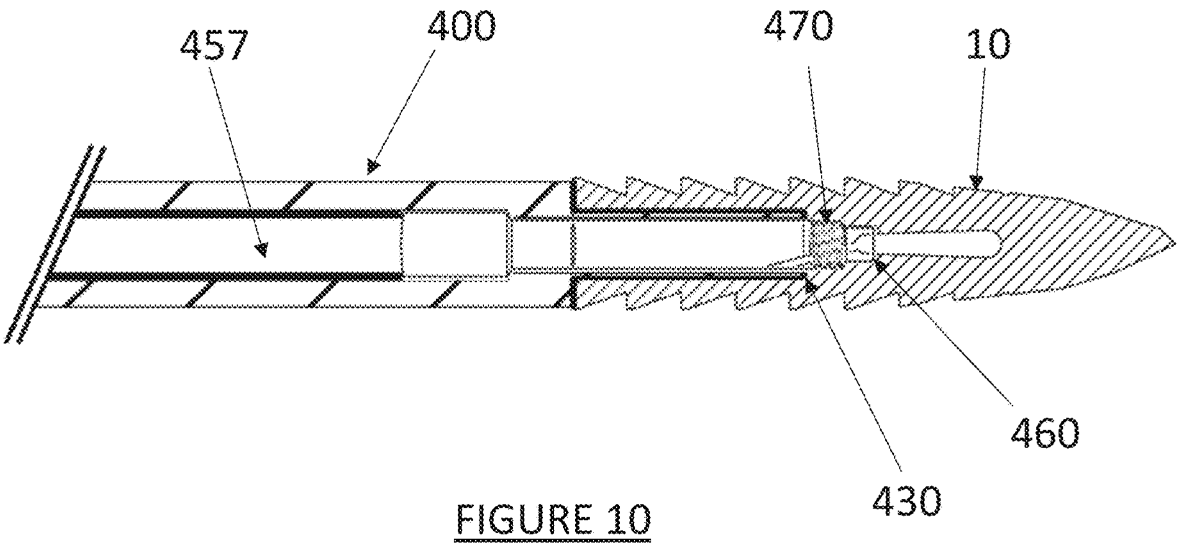
FIG. 10 depicts a suture anchor secured to the insertion and deployment tool of FIGS. 8A through 8D.

FIGS. 8A through 8D depict one exemplary embodiment of an insertion and deployment tool 400 which is engageable with the anchor 10 to deploy the anchor in bone, including the various suture anchor embodiments described herein. In this embodiment, the tool 400 includes a proximal handle 410, a central shaft 420, and a distal tip section 430. As best seen in FIG. 8B, the distal tip section 430 can include a generally cylindrical engagement tip 433, with a central cannula 435 extending therethrough. FIGS. 9A and 9B depict a threaded blocking device or inner shaft tool 450 which fits within the central cannula 435 in the deployment tool 400, the inner shaft tool 450 desirably including a proximal cap 455, an elongated body 457, a blunt terminal distal tip 460 and a threaded portion 470, with the distal tip 460 and threaded portion 470 desirably sized and configured to fit within the tunnel 60 of the anchor 10, allowing the threaded portion 470 to be engaged with and retain the internally threaded portion 130 of the tunnel 60. When the deployment tool 400 and inner shaft tool 450 are fully assembled in this manner, the distal ends of the tool 400 and shaft tool 450 will desirably extend within the tunnel 60 and secure the anchor to the tool 400 in a desired manner.

The disclosed deployment tool 400 and associated inner shaft tool 450 include several important features which contribute to the innovative functions of Applicant’s system. In particular, the blunt terminal distal tip, in the initial deployment stage, allows the suture to move freely through the anchor, by inhibiting and/or preventing the suture from entering the locking slits. The deployment tool and inner shaft tool also significantly increase the rigidity and strength of the attached anchor by extending through the hollow tunnel of the anchor body during initial deployment. The central shaft and distal tip section desirably transmit much of the insertion force from a mallet to the anchor during initial deployment. Rotation of the inner shaft tool 450 desirably unthreads the threaded portion with the internally threaded portion 130, which retracts the blunt terminal distal tip to allow for unblocking of some or all of the locking slits and/or removal of the inner shaft tool and/or the deployment tool after final deployment.

Surgical Procedure

In at least one exemplary procedure, the anchor 10 can be deployed in a suitable bone site by first passing the suture or tape through soft tissue requiring repair (i.e., through the rotator cuff or other tissue). Alternatively, soft tissue itself might be anchored directly in place within a desired bone site, rather than using suture, in which case the tissue could be manipulated in the same way as the suture to be described in this explanation. For this reason, though the term "suture" is used throughout this specification, for convenience, the term should be considered sufficiently broad to include other media having similar functional characteristics, including soft tissue itself. A pilot hole can be drilled or punched into the attachment site, through the cortical bone layer and into a cancellous bone layer. In some circumstances, an optional metal distal tip may be employed with the anchor, in which case the step of drilling a pilot hole might be unnecessary. The suture can be fed through a suture eyelet, directly or with a snare. One or more suture ends may be placed through the eyelet.

With the anchor and associated attached insertion device(s) positioned at a desired bone site, initial deployment of the anchor can occur. To initiate this initial deployment, a mallet can be driven against the proximal end of the handle portion to drive the anchor distally to its initial deployment position. In at least one exemplary embodiment, the anchor can be driven approximately ⅓ to ⅔ of its length into the targeted bone, while in other embodiments a different depth could be obtained. If desired, the anchor can include a visual and/or tactile indicator of a recommended initial depth, such as a first rib section, laser line or colored rib section 490 (see FIGS. 4A and 4B). Once the anchor is in a desired position, the surgeon may draw tension on the suture to pull or otherwise manipulate the soft (or other) tissues to a desired position and/or tension.

Once a desired tension is achieved, the threaded blocking device can be displaced a desired amount, such as by partially and/or fully unthreaded the blocking device from the internally threaded portion 130 within the anchor. When the blocking device is displaced, this pulls the blunt terminal distal tip 460 in a proximal direction, exposing a distal portion of one or more slits to the suture, which desirably allows the suture to be pulled into a desired position within the one or more slits. In various embodiments, however, the differential slit angles and/or the continued presence of at least a portion of the blocking device desirably prevent the suture from travelling fully up into a locked position within the opposing slit, which in this embodiment is on the tissue-side of the anchor body, allowing the surgeon the freedom to lock and/or unlock the suture into a single locking point as desired to draw and/or release tension.

Once a desired tension has been obtained, final deployment steps can be initiated by fully removing the threaded blocking device and malleting the inserter handle until the anchor rests at or below the surface of the bone. This desirably causes the suture to travel up into both slits on the anchor body. Because the suture desirably maintains an equilibrium position relative to the surface of the bone during post-tensioning and final anchor deployment, the tension in the suture is desirably maintained constant during final deployment of the anchor. If additional tension is required, the anchor can optionally be rotated to provide an incremental or "fine-tuned adjustment" of tension, or the blocking device could be reinserted to release the suture, and/or the anchor could be malleted deeper into the bone, pulling the suture ends with it, thereby increasing tension.

Once fully deployed, the suture can desirably be pinched between one or more suture barbs and the surrounding bone on the tissue side of the anchor, and also pinched or wedged within the suture slits on both sides of the anchor body. Finally, the free suture ends can be pinched or wedged between the suture barbs and the surrounding bone opposite to the tissue side of the anchor, thereby potentially creating four points of suture attachment. If desired, the anchor could also be rotated to desirably engage and/or disengage various portions of the suture and rib sections proximate to the grooves of the anchor. Once the desired anchor attachment is attained, the handle and attached insertion device can be removed and the procedure completed.

In at least one alternative embodiment of a surgical procedure, such as during insertion of a suture anchor, the suture anchor 10 can be positioned over the distal tip section 430 of the tool 400, with the internally sliding blunt terminal distal tip 460 of the inner shaft tool 450 desirably extending within the tunnel 60 some distance proximal to the locking slits, and the threaded portion 470 engaged with the internally threaded portion 130. This arrangement thereby secures the anchor 10 to the tool 400, and also desirably blocks and/or interferes with at least a portion of the one or more locking slits to inhibit and/or prevent the suture or tape from partially and/or fully engaging with one or both locking slits of the anchor. In this manner, the suture or tape can desirably be passed freely through the anchor until a desired tension is applied or pulled by a surgeon or other medical professional.

The employment of a threaded blocking device in this embodiment, which allows engagement with corresponding threads formed within the anchor, will desirably significantly increase the strength and stability of the anchor and deployment tools, as well as allow for the transmission of significant impaction forces from the handle to the anchor during anchor insertion. This arrangement can also facilitate disengagement between the anchor and the handle when desired, as the handle can be easily removed from the anchor at any time after the blocking mechanism is unthreaded and/or removed.

Initially, an opening in a targeted bone or other anatomy can be prepared, and the proximal tip and some portion of the body of the anchor can be provisionally inserted into the targeted anatomy. The surgeon can then apply a correct tension on the suture or tape, which includes the ability to freely advance and withdraw the suture(s) and/or tape(s) through the suture slot of the anchor. If desired, the surgeon can rotate or otherwise manipulate the inner shaft tool 450, which desirably draws the internally sliding blunt terminal distal tip 460 (i.e., the "blocking" element) of the inner shaft tool 450 towards a proximal end of the anchor and, depending upon the amount of rotation, can withdraw the terminal distal tip 460 to a position proximal to the one or more locking slits of the anchor, thereby allowing the suture to be partially and/or fully drawn into one or more of the locking slits and inhibiting further transverse motion of the suture relative to the anchor (i.e., locking the suture in the anchor).

If desired, the terminal distal tip 460 may be fully withdrawn from the anchor at any point, which can then fully expose the locking slits to the suture and allow locking of the suture(s) in a desired manner. If unlocking of the sutures is desired, the terminal distal tip may be reinserted into the anchor, which will allow the blunt terminal distal tip 460 to contact the suture(s) and potentially "push" the suture out of the one or more locking slits, thereby "unlocking" the suture and allowing the surgeon to alter the tension of the suture to a new desired level and/or position. Subsequent withdrawal of the blunt terminal distal tip 460 from the tool can then allow the suture to travel back into the locking slits and lock the suture. This process can be repeated multiple times until a desired tension and/or positioning of the suture has been achieved.

Once a desired suture tension has been achieved, the anchor may be fully seated within the targeted anatomy. In at least one exemplary surgical procedure, the terminal distal tip 460 can be repositioned, slid, displaced and/or otherwise altered and/or removed from the cannulated handle (which can include removal of the inner shaft tool 450 from the tool 400, if desired). The suture or tape can then be pulled into at least one of the locking slits, desirably "locking" the tape or suture into place. As previously noted, if the surgeon desires to alter tension of the suture or tape, the surgeon need merely push the suture towards the distal end of the anchor, which desirably disengages the locking slit and allows the surgeon to re-tension the suture or tape to a desired level. However, once a "final" suture tension and/or positioning has been obtained, the anchor can be tapped fully into the bone to a "final" position. During this action, the sliding motion of the anchor's outer surface against the inner bore of the bone will desirably draw the suture or tape into a posterior portion of the adverse oblique slit of the anchor, which then allows the suture or tape to engage completely with the suture or tape, thereby locking the suture or tape into the anchor.

In at least one alternative exemplary embodiment, a suture anchor can be pre-loaded with suture or tape, and then inserted fully into the bone, with the surgeon subsequently pulling on the suture to tension and/or loosen the suture a desired amount. When a desired tension is obtained, the blunt terminal distal tip 460 or other "blocking" feature can be repositioned, slid, displaced and/or otherwise altered and/or removed from the cannulated handle, which can allow the suture or tape to travel into and lock within the locking slits (i.e., by manual tension induced by the surgeon or by rebounding tissue) as previously described. If the surgeon wishes to alter tension of the suture or band, the blocking piece can be reintroduced into the cannulated handle and anchor, which desirably forces the suture or tape out of the locking slits, allowing the surgeon to easily reposition and relock the suture or tape as desired.

The disclosed designs can desirably accommodate a variety of surgical techniques and/or surgeon preferences, including the tensioning of the suture to a desired degree before and/or after final seating of the anchor, if desired. For example, a surgeon can choose to partially implant the anchor with the suture in the anchor, tension the suture(s) and remove the blocking inner sleeve to provisionally "cinch-lock" the suture within a single slit, and then fully seat the anchor into the bone with the suture locking into both slits without over-tensioning. Alternatively, the surgeon may choose to first fully implant the anchor and attached sutures into the bone, and then the surgeon can tension or release the sutures to a desired degree (because the sutures could desirably be prevented from locking into the slits by the partially and/or fully inserted blocker). Once a desired tension is obtained, the blocking inner sleeve can be removed, and the surgeon can "cinch-lock" the sutures on both sides of the anchor by simply pulling up on the sutures.

Desirably, the design, position and/or angulation of the adverse oblique slit and related features of the suture anchor permit the anchor to be advanced further into the bone (after the initial suture tension has been obtained) without significantly altering the tension and/or positioning of the portion (s) of the suture attached to the targeted soft tissue. More specifically, the disclosed design desirably allows the suture anchor to be advanced into the bone a desired amount (i.e., during final "seating" of the anchor) without increasing and/or decreasing the suture tension an appreciable amount, which is a significant improvement over existing suture anchor designs. Moreover, the present suture anchor design potentially allows a surgeon to unlock and change the suture tension at any point during the surgical procedure, even after the suture anchor has been fully seated within the targeted bony anatomy. In various embodiments, surgical techniques can be employed to selectively lock and/or unlock one or both sides of the locking slits, which can include simple one-handed manipulation of the suture or tape (i.e., by pushing/pulling the suture towards and/or away from the distal tip of the anchor). This anchoring feature allows locking and/or unlocking of the suture and/or tape without requiring additional surgical tools, without taking extra operating time to engage/disengage the locking mechanism and/or without damaging and/or weakening the suture and/ or tape, the anchor and/or the surrounding bony anatomy.

In the various embodiments disclosed herein, the suture anchors and associated tools desirably incorporate multiple locking features that facilitate locking on two sides of the suture anchor, giving it a dual locking mechanism, with one or both sides desirably being independently lockable in various embodiments. This arrangement represents a significant improvement over many existing knotless anchor designs, which primarily rely on the anchor to bone interface to wedge and secure the tape held between the anchor and the bone. The disclosed designs also allow for an anchor to enter the bone, and then subsequently allows a surgeon to pull and/or relax the suture to a desired tension through the anchor, with the surgeon subsequently partially withdrawing and/or fully removing the internal handle piece which "blocks" the oblique slit, allowing the locking mechanism(s) to provide some level of locking of the suture or tape to the anchor and/or surrounding bone. Once the blocking tool is displaced or otherwise "removed" from the first position, the suture or tape can be pulled into the primary locking slot of the anchor then optionally impacted into the bone. When impacted, the suture or tape will then be pulled/pushed into the secondary oblique slit which acts as a secondary locker. The oblique slit in various embodiments is desirably adverse, which gives it a solid lock within the anchor, and which also provides sufficient "slack" in the suture or tape to prevent over tensioning of the suture during the final bone impaction procedure. The unique opposing alignment of the locking slits in various embodiments desirably prevents and/or inhibits unwanted locking of both slits, when desired.

In various exemplary embodiments, the adverse oblique slits and related anchor components can allow the suture to also be supplementally engaged between at least one rib of the suture anchor and the bony surface once the suture is fully locked within the anchor, thus providing an additional locking element for suture securement. In various preferred embodiments, the suture anchor comprises external surface features for securing the implant within surrounding bone. These external surface features can comprise bone barbs, threads, projections and/or similar features. If desired, suture barbs could be disposed on the outer surface of the body at proximal and/or distal end(s) thereof, for clamping suture or tissue between the outer surface of the body and adjacent bone. If desired, bone displacement tabs could be disposed on a proximal and/or distal portion of the implant body, for displacing bone distal to suture for allowing optimal suture sliding during initial deployment of the anchor Desirably, the disclosed designs of the adverse oblique slits and related anchor components allow the suture to pass along flattened sections of the ribs prior to the final suture locking step, yet allow the suture to be "locked" in the interface between the anchor and the bony anatomy once the suture is fully drawn into the locking slit. As best seen in FIGS. 11A through 11D, a suture anchor 500 can include a suture or tape 510, which aligns with a suture recess or grooved section 520 of the anchor ribs 530 when the suture 510 resides within the slot 540. However, when the suture slides in a posterior direction down the locking slit 550 (i.e., during final locking of the suture), the oblique angle of the locking slit can tend to draw the suture 510 out of the grooved section, and into a location sandwiched by one or more anchor ribs 530 and the bony surface of the surrounding anatomy (see FIGS. 11C and 11D). Because the posterior tip of the locking slit is positioned outside of the grooved section, therefore, the suture can lock between one or more ribs and the bony anatomy (including on one or both sides of the anchor), providing additional supplemental anchoring of the suture.

This arrangement of the slits, which allows the suture to exit the top of the slit proximate to at least one ridge of the anchor, can enhance the locking mechanism, as this arrangement can direct the sutures to the ribs of the anchor that are not cut out, so there is enhanced friction of suture between and/or along ribs of anchor and bone. This desirably limits and/or inhibits the suture from remaining within the beveled out areas on the sides of the anchor (where the ribs are more shallow and allow for sliding during tensioning step). The angling of the slits pushes the sutures to the non-beveled out areas of the anchor. If desired, rotation of the anchor in a desired direction can cause one of more of the "interrupted" ribs to engage and/or disengage the suture after the anchor has been fully seated.

In addition, the anchor can include at least one posterior rib 555, which does not include a grooved section. As best seen in FIG. 11C, this posterior rib 555 will desirably engage the suture between the rib and the surrounding bone, providing a final locking feature for the suture.

In the exemplary embodiment of FIG. 11A, it can also be seen that the final ring 525 (i.e., the proximal ring) can optionally not include a grooved section. While many existing anchors utilize numerous full rings (i.e., a series of full circumferential rings without a groove) to lock the suture into the bone/anchor interface, a concern among surgeons exists that such an arrangement (i.e., multiple full rings) might grab or retain and "bunch" the suture(s) in an unwanted manner when the anchor is being impacted into the bone, which can significantly alter the final suture tension as well as potentially damage and/or abrade portions of the suture located between the bone/implant. For example, where each ring is approximately 2 mm apart (measured longitudinally), each groove (without an opening, slot or grooved portion) can pull associated suture sections down into the bone at differing positions and/or tensions as the anchor is impacted, giving unwanted tension to the cuff. This often leads to slight tearing of the cuff because of over tensioning.

In contrast, the disclosed embodiment of FIG. 11A includes a pair of grooves that extend up the sides of the anchor to the final ring (i.e., the posterior rib 555). This design allows the surgeon to tension the suture and attached anchor with up to 20 mm of the anchor already inserted into the bone. The final 2 mm ring is desirably a full ring which can act as a supplemental locking device (i.e., compressing the suture between the ring and the bone), but this single ring will desirably not pull on the suture and cuff in an undesired fashion. Unlike most designs which rely upon numerous longitudinally spaced full rings to lock the suture between the bone/ring interface of the anchor, the present embodiment can rely upon other locking mechanisms (i.e., internal and/or external mechanisms described in various sections herein, including the adverse oblique slit arrangement) for primary locking of the suture to the anchor, and thus the need for multiple ring locking into the bone is not absolutely necessary to proper functioning of the present design. However, the presence of the full final ring can desirably act as a final locking mechanism (i.e., a supplemental locking mechanism) to lock the suture to the external surface anchor without incorrectly tensioning the cuff and/or damaging the suture, which results in an anchor design having multiple internal and/or external suture locking features, allowing for redundant and robust locking of the suture to the anchor.

Figure 12A:
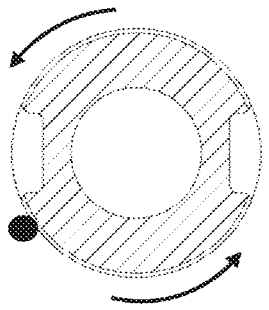
FIGS. 12A and 12B depict one exemplary suture unlocking procedure.
Figure 12B:
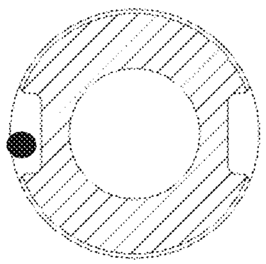

Another unique feature of the disclosed suture anchor designs is the ability for a surgeon to selectively "lock" and/or "unlock" the supplemental fixation between the anchor ribs and the bony anatomy. FIGS. 12A and 12B depict one exemplary embodiment wherein the supplemental fixation between the suture and the rib/bone can be released by counterclockwise rotation of the suture anchor. If desired, such rotation could be utilized in conjunction with deployment of a blocking tool to release suture fixation with the anchor (as previously described), allowing the surgeon to alter suture positioning and/or tension. Once a desired tension is obtained, the blocking tool could be removed, the suture could be relocked, and the anchor could be rotated clockwise to reengage the supplemental fixation.

If desired, rotation of the suture anchor could also be utilized to tighten and/or otherwise adjust suture tension in a desired manner, in that anchor rotation could pull additional suture into the fixation hole. This grants a surgeon the ability to "fine-tune" the tension of the suture or tape by rotating or twisting the anchor to some degree within the bone, allowing for small increases and/or decreases in the length and/or tension of the anchor—for 'fine' control of suture and/or tape tension. The angling and fine tuning of tension mentioned previously also allows surgeon to encourage the sutures to enter the slit by twisting or "dialing in" the anchor, instead of always having to push the anchor in further into the bone.

In comparison to existing suture anchor systems, the disclosed systems and devices are significantly more robust and incorporate significantly fewer parts. Moreover, the surgical techniques for using the disclosed anchors and associated deployment systems described herein is somewhat similar to those of exiting systems, in that the initial start of the surgery involves similar steps to those of traditional knotless anchor fixation, allowing a surgeon to utilize the disclosed devices with minimal instruction. The surgeon can partially tap the suture anchor into a targeted bone and then manually tension the suture (which may already be engaged at the other end with other tissue) through the knotless slot. The present systems and designs, however, grant the surgeon much greater flexibility in holding the tension of the anchor where the surgeon desires, as well as allow the surgeon to easily adjust tension (i.e., increase and/or decrease tension) as many times as the surgeon desires and at almost any point during the surgery. The disclosed systems allow the surgeon to obtain a correct tension, and then easily disengage or otherwise manipulate the blocker (which can desirably be threaded into the anchor). In various embodiments, the threaded blocker not only holds the anchor onto the non-disposable handle, but also desirably blocks the unique locking mechanism. The handle and associated blocker can comprise a two-piece design, with one component extending into the back of (and through a cannulation in) the non-disposable handle. Once the back-locking piece is manipulated, displaced and/or otherwise removed, the surgeon can quickly "lock" the tension in the suture/tape by pulling the suture/tape into the oblique locking slit proximate to the hand holding the suture. The "cross-angled" design of the locking slits allows the suture to wedge and lock initially on one side of the anchor, without causing the suture to also travel up and lock into the opposing locking slit in an undesired manner (i.e., the side away from the surgeon's hand holding the suture). Because of this, the surgeon can easily "unlock" the suture by simply pushing the suture towards the bone and/or distal tip of the anchor, drawing the suture out of the locking slit and allowing the suture to freely pass back into the larger slot. Once tension has been altered, the suture can be relocked simply by pulling up on the suture. The surgeon can repeat this activity as desired-unlocking and relocking the suture by pushing the suture down and pulling the suture up. Because of the unique oblique transverse slots, the other side of the anchor is desirably not locked at an unwanted point (i.e., only one side of the anchor need be locked at this point). This one-sided locking system gives the surgeon an easy way to lock the desired tension right where he or she likes by just pulling up. The other side of the anchor will desirably fully engage when the anchor is tapped down all the way into the bone. Once this second locking action occurs, the suture can be fully locked, with the suture secured to the anchor by two or more independent locking mechanisms, as well as being wedged between various portions of the anchor rib and the bone.

The unique arrangement of the slots and non-aligned slits in the disclosed anchor design also provides an opportunity for some predetermined amount of additional "slack" in the suture/tape to exist, which can be "taken up" when the anchor is fully seated into the bone. When a traditional knotless anchor is seated into the bone after being pre-tensioned, the final seating movement of the anchor further into the bone will often tend to draw some additional suture along with the anchor, increasing the tension in the suture and potentially over-tensioning the rotator cuff. Because of this concern, many surgeons will under-tension the suture to some limited degree, hoping that the final seating action of the anchor will cause the suture to reach a proper tension. Unfortunately, such guess work can often lead to under-tensioning of the suture.

Figure 13A:
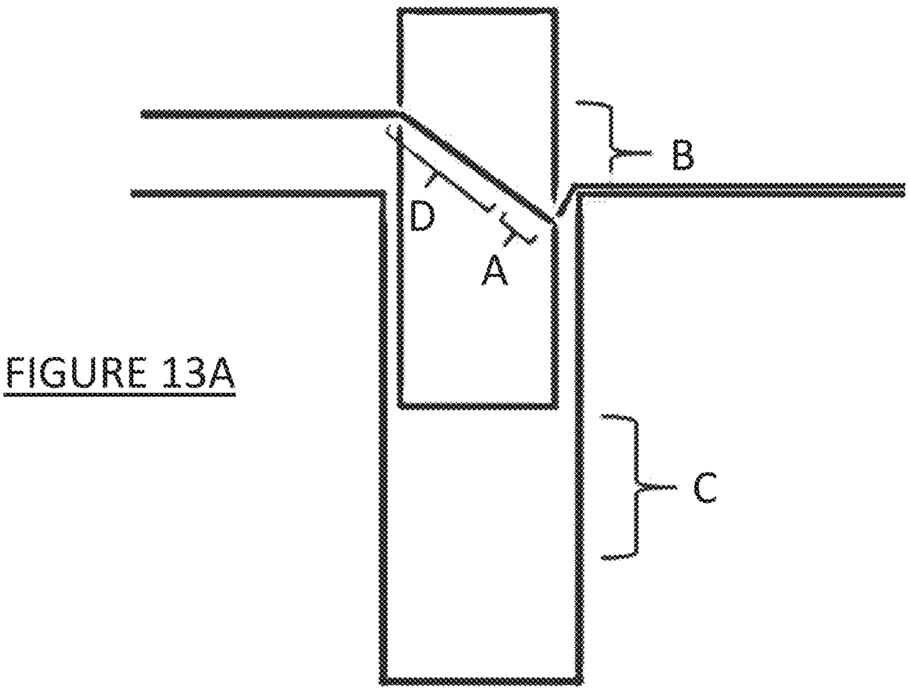
FIGS. 13A and 13B graphically depict how one exemplary arrangement of the locking slits in a suture anchor design can allow advancement of the anchor with little or no disturbance of the suture tension.
Figure 13B:
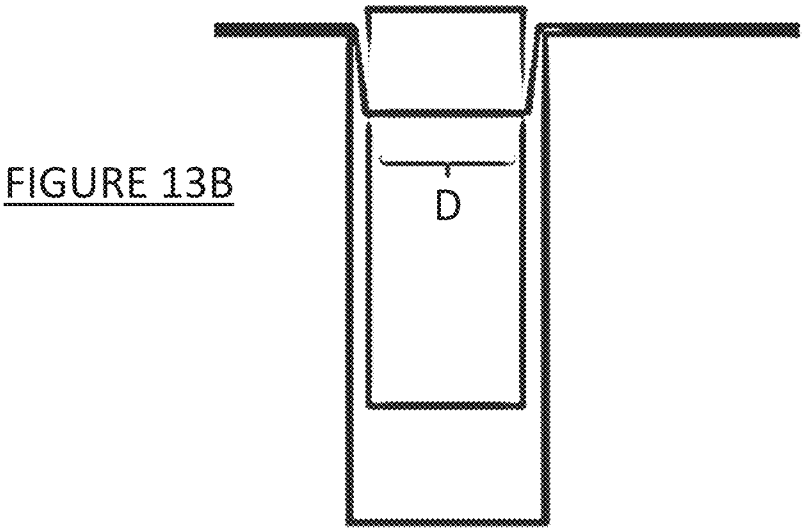
Figure 14:
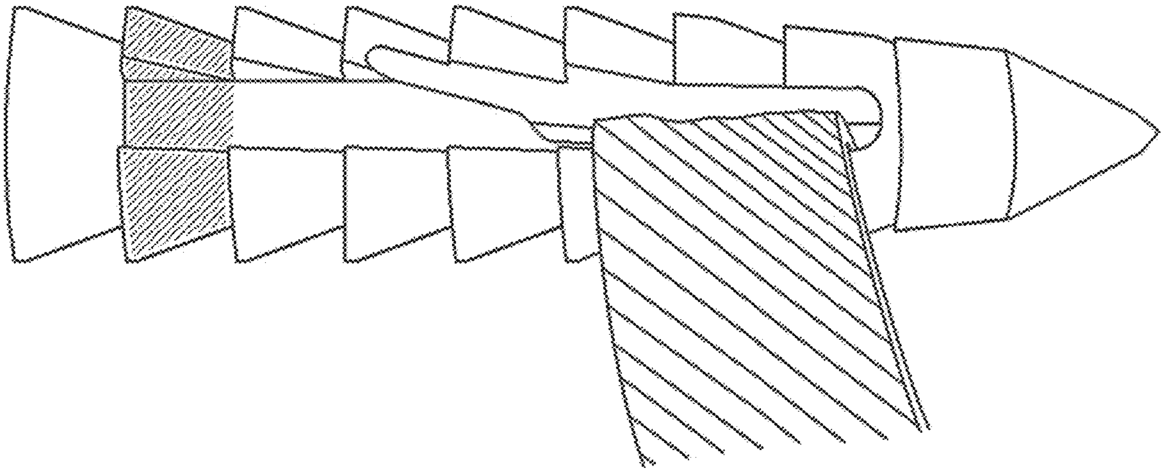
FIG. 14 depicts a side view of an anchor with suture tape extending through a slot therein.

FIGS. 13A and 13B depict one example of how the unique arrangement of the locking slits in the disclosed design can desirably result the suture being "angled" to some degree while provisionally locked with the anchor by the surgeon, which slightly increases the length of the suture within the anchor by an amount "A" as compared to a completely flattened suture length D. When the anchor is being fully seated into the bone, the movement between the anchor and the surrounding bone will desirably impel the suture to move up into the opposing slot an amount "B", and also pulls the amount of slack "B" out of the suture (as it flattens across both slits), which allows the anchor to be pushed a distance "C" into the bone (i.e., A+B=C) without significantly altering the tension and/or positioning of the suture.

In various embodiments, the inner sleeve blocker can greatly improve surgeon flexibility in placing and tensioning the sutures—with the present systems providing both 'gross' and 'fine' control of the suture tensioning and/or positioning. Gross control can be accomplished by pulling the sutures, while fine control can be accomplished by twisting of the suture anchor. The threaded engagement between the insertion tools and the anchor desirably ensures control over the anchor as it slides down the sutures and is pushed into the bone so that the anchor will not inadvertently 'fall off' the inserting handle. With the different angles of the slits as the suture is pushed into the slit, the body of the anchor can desirably itself "bend or flex" outward to some small degree (i.e., when the sutures are fully within the slits), desirably increasing the dimeter of the seated anchor within the bony aperture and further enhancing pullout strength. Moreover, with the two different locking slits occupying different planes as compared to locking slits that are parallel to each other and/or that may be aligned with a longitudinal axis of the anchor, the "pull-up" forces acting on the suture (and thus on the suture anchor) are desirably spread across more than one plane of the anchor. This locking mechanism creates an extremely strong bond with the bone—as in order to 'loosen' it once seated in the cinch, two different directions of force would be needed, which is less likely to occur during placement or afterwards.

Another unique feature of the disclosed system is the ability to insert the inner blocking sleeve back into the tool and suture anchor at any point during the surgical procedure, which will "un-cinch" and desirably loosen and/or unlock the sutures, which could facilitate removal of the anchor (if desired) as well as an opportunity to re-tension (i.e., by reintroducing into the anchor and pushing the sutures out of the slits).

In at least one exemplary surgical technique, the disclosed knotless anchor could be used for the reattachment of soft tissue to bone. For example, in one primary surgery the disclosed suture anchor and related deployment tools could be used for rotator cuff repairs. During such a procedure, the suture or tape can be passed with a suture passer through the rotator cuff, with the limbs loaded back into the knotless anchor. The suture limbs can then be pulled through the anchor with a suture passer or suture loop. A pilot hole for the anchor can be made in the targeted bony anatomy, which is typically made by malleting an awl into the bone to a depth equal to a desired depth (i.e., a laser line in the suture anchor). This action desirably creates an opening for the anchor to enter the bone. The tip of the suture anchor can be inserted into the pilot hole while holding light tension on the sutures, with the anchor malleted approximately 5 mm or 10 mm (or some other desired amount) into the bone. The surgeon can now pull his or her desired tension on the cuff, with light pressure desirably placed on the handle while pulling the desired tension. Once the desired tension is achieved, the threaded locking mechanism located on the end of the non-disposable handle can be withdrawn to some degree (and/or removed) by turning the threaded end piece counterclockwise. This action will desirably unlock some or all of the anchor from the handle and open the blocking mechanism. The surgeon can now provisionally lock the tension by pulling the suture upwards.

Upon provisional locking, the anchor and attached suture or tape is ready to be malleted fully into the bone. As the anchor is being fully malleted, the suture or tape on the opposing side of the suture anchor (i.e., the "unlocked side") will desirably be guided into the second locking mechanism located on the opposite side of the primary locker. This suture lock will desirably only be engaged once the anchor is fully seated. Once fully seated, the tool handle can then be removed by simply pulling it off of the anchor, and the procedure is completed.

If desired, the disclosed knotless anchor could include a proprietary locking mechanism that allows for tensioning of the cuff, and then locking of the tension.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention.

All references, including publications, patent applications, and patents, cited herein are hereby incorporated by reference to the same extent as if each reference were individually and specifically indicated to be incorporated by reference and were set forth in its entirety herein.

The various headings and titles used herein are for the convenience of the reader and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms “a” and “an” and “the” and similar referents in the context of describing the invention are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., “such as”) provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An anchoring system for securing tissue to bone, comprising an implant comprising a body having a longitudinal axis, a longitudinally extending lumen extending within at least a portion of the body, a suture eyelet extending transversely through the body with at least a portion of the suture eyelet being in fluid communication with the longitudinally extending lumen, and a first suture pinch slit and a second suture pinch slit, each of the first and second suture pinch slits positioned at a proximal end of a suture recess, wherein the first suture pinch slit is non parallel to the longitudinal axis and is also non parallel to the second suture pinch slit.

2. The anchoring system of claim 1, wherein the body further includes the suture recess extending posteriorly along a first portion of a length of the body having a first predetermined depth below an outer surface of the body, the first suture pinch slit having a first end located within the suture recess.

3. The anchoring system of claim 2, wherein the body further includes a second suture recess extending posteriorly along a second portion of a length of the body having a second predetermined depth below the outer surface of the body, the second suture pinch slit having a second end located within the second suture recess.

4. The anchoring system of claim 1, wherein the suture eyelet extends along at least 20% of a longitudinal length of the implant body.

5. The anchoring system of claim 1, wherein at least a portion of the longitudinally extending lumen includes an internally threaded section.

6. The anchoring system of claim 5, wherein the internally threaded section is adapted for receiving an insertion device, the insertion device including an externally threaded portion for engagement with the internally threaded section.

7. The anchoring system of claim 6, wherein the insertion device includes a distal blocking section that blocks the first suture pinch slit without fully blocking the suture eyelet when the externally threaded portion is engaged with the internally threaded section.

8. The anchoring system of claim 7, wherein the implant further comprises external surface features for securing the implant within surrounding bone.

9. The anchoring system of claim 8, wherein the external surface features comprise bone barbs.

* * * * *